(12) United States Patent
Hatori et al.

(10) Patent No.: US 10,307,103 B2
(45) Date of Patent: Jun. 4, 2019

(54) PAD FOR ELECTRODES

(71) Applicant: SEKISUI PLASTICS CO., LTD., Osaka (JP)

(72) Inventors: Takaaki Hatori, Inashiki-gun (JP); Yasuaki Shioyama, Inashiki-gun (JP); Kazuhiro Yoshikawa, Tokyo (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 0 days.

(21) Appl. No.: 15/526,858

(22) PCT Filed: Sep. 30, 2015

(86) PCT No.: PCT/JP2015/077727
§ 371 (c)(1),
(2) Date: May 15, 2017

(87) PCT Pub. No.: WO2016/080082
PCT Pub. Date: May 26, 2016

(65) Prior Publication Data
US 2017/0332967 A1    Nov. 23, 2017

(30) Foreign Application Priority Data

Nov. 17, 2014  (JP) ................................. 2014-233169
Mar. 31, 2015  (JP) ................................. 2015-074416

(51) Int. Cl.
*A61B 5/0408*    (2006.01)
*A61B 5/0492*    (2006.01)
(Continued)

(52) U.S. Cl.
CPC .......... *A61B 5/6833* (2013.01); *A61B 5/0478* (2013.01); *A61B 5/04087* (2013.01);
(Continued)

(58) Field of Classification Search
CPC ... A61B 2562/247; A61B 5/04; A61B 5/6833; A61B 5/04087
(Continued)

(56) References Cited

U.S. PATENT DOCUMENTS 4,391,278 A * 7/1983  Cahalan ............. A61B 5/04087
                                                  600/391
4,779,630 A * 10/1988 Scharnberg ............ A61N 1/046
                                                  607/142
(Continued)

FOREIGN PATENT DOCUMENTS

EP    1 739 149    1/2007
EP    1 958 568    8/2008
(Continued)

OTHER PUBLICATIONS

International Search Report dated Dec. 8, 2015 in International Application No. PCT/JP2015/077727.
(Continued)

*Primary Examiner* — Lee S Cohen
*Assistant Examiner* — Erin M Cardinal
(74) *Attorney, Agent, or Firm* — Wenderoth, Lind & Ponack, L.L.P.

(57) ABSTRACT

A pad for electrodes (1) including a first conductive adhesive sheet (2) for connection with an electrode, a second conductive adhesive sheet (4) for connection with another electrode, the second conductive adhesive sheet positioned to be spaced apart from the first conductive adhesive sheet in a planar direction of each conductive adhesive sheet, and a base (10) supporting the first conductive adhesive sheet and the second conductive adhesive sheet. At least one surface of each of the first conductive adhesive sheet and the second conductive adhesive sheet is exposed, and each of the first conductive adhesive sheet and the second conduc-
(Continued)

tive adhesive sheet has a thickness compressibility of 10% or less and a thickness recovery ratio of 95% or more. The base is a non-electroconductive base having a water absorption capacity of 1 to 1.5 times, and the pad has a moisture permeability of 1,000 g/m²/24 h or more.

11 Claims, 3 Drawing Sheets

(51) Int. Cl.
    *A61B 5/00*     (2006.01)
    *C09J 9/02*     (2006.01)
    *C09J 133/26*     (2006.01)
    *C09J 7/21*     (2018.01)
    *A61B 5/0478*     (2006.01)

(52) U.S. Cl.
    CPC ............... *A61B 5/0492* (2013.01); *C09J 7/21* (2018.01); *C09J 9/02* (2013.01); *C09J 133/26* (2013.01); *A61B 5/0408* (2013.01); *C09J 2433/00* (2013.01)

(58) Field of Classification Search
    USPC .................................................. 600/391–392
    See application file for complete search history.

(56) References Cited

U.S. PATENT DOCUMENTS

| | | | |
|---|---|---|---|
| 5,674,561 A * | 10/1997 | Dietz | A61F 13/023 427/208.4 |
| 5,891,028 A * | 4/1999 | Lundback | A61B 5/0408 600/387 |
| 6,055,452 A * | 4/2000 | Pearlman | A61B 5/0536 600/547 |
| 6,115,638 A * | 9/2000 | Groenke | A61N 1/0492 600/392 |
| 6,694,193 B2 * | 2/2004 | Lyster | A61N 1/046 607/142 |
| 7,162,291 B1 * | 1/2007 | Nachaliel | A61B 5/05 600/393 |
| 8,263,720 B1 | 9/2012 | Salamone et al. | |
| 2002/0026229 A1 * | 2/2002 | Weil | A61N 1/046 607/142 |
| 2008/0200793 A1 * | 8/2008 | Furue | A61B 5/0537 600/393 |
| 2010/0081913 A1 * | 4/2010 | Cross | A61B 5/04085 600/386 |
| 2011/0319787 A1 * | 12/2011 | Lamoise | A61B 5/103 600/549 |

FOREIGN PATENT DOCUMENTS

| | | | | |
|---|---|---|---|---|
| EP | 2 767 632 | | 8/2014 | |
| EP | 3222212 A4 * | | 8/2018 | ........... A61B 5/0492 |
| JP | 4-246371 | | 9/1992 | |
| JP | 2003-313304 | | 11/2003 | |
| JP | 2003-346554 | | 12/2003 | |
| JP | 2011-45816 | | 3/2011 | |
| WO | 2014/039525 | | 3/2014 | |

OTHER PUBLICATIONS

Extended European Search Report dated Jul. 30, 2018 in European patent Application No. 15861928.8.

\* cited by examiner

PAD FOR ELECTRODES

TECHNICAL FIELD

The present invention relates to a pad for electrodes. Priorities are claimed on Japanese Patent Application No. 2014-233169, filed on Nov. 17, 2014, and Japanese Patent Application No. 2015-074416, filed on Mar. 31, 2015, the contents of which are incorporated herein by reference.

BACKGROUND ART

Pads for electrodes have conventionally been used for apparatuses such as electrocardiograph apparatuses, electroencephalograph apparatuses, and electromyograph apparatuses, which extract and measure electrical signals from subjects to be measured.

For example, PTL 1 discloses a biomedical pad for electrodes provided with a hydrous gel layer and using the hydrous gel layer in close contact with a living body surface. In addition, PTL 2 discloses a polymer hydrogel electrode provided with a conductive polymer hydrogel and an electrode element, which is used with the conductive polymer hydrogel being attached to a human body and a surface of an object.

CITATION LIST

Patent Literature

[PTL 1] Japanese Unexamined Patent Application, First Publication No. H04-246371
[PTL 2] Japanese Unexamined Patent Application, First Publication No. 2003-346554

SUMMARY OF INVENTION

Technical Problem

In recent years, with ongoing progress in development of apparatuses such as electrocardiographs that are compact and have multifunction, and with increasing concern toward health, a trend has emerged to acquire biological information such as electrocardiograms using compact biometric sensors not only in hospital examinations, medical examinations, or the like, but also in daily life, and to use the biological information for health maintenance and management.

Such compact biometric sensors for use in daily life have two or more electrodes for acquiring electrical information such as electrocardiograms, which are positioned adjacent to each other within the same device.

The use of a conventional electrode pad for fixing such a compact biometric sensor to a subject of measurement is accompanied by a risk of short circuit caused by the contact between the adjacent electrodes via the electrode pad.

In addition, for avoiding such a short circuit, it is necessary to attach electrode pads to respective electrodes of the biometric sensor and to apply each of the electrode pads to the subject while avoiding the contact between the electrode pads, whereby the handling of the electrode pads is rendered troublesome.

Furthermore, the electrode attached to the electrode pad detects the electric signal emitted from the living body or the like via the electrode pad. In this process, the resistance of the pad for electrodes fluctuates by, for example, deformation of the electrode pad due to external force or the like, or absorption of water vapor such as sweat by the electrode pad, which prevents accurate transmission of the electric signal emitted from the living body to the electrodes, and thus becomes an obstacle to stable measurement.

Furthermore, the electrode pad is required to give good feel when used which does not cause stuffiness or rashes when adhered to the skin.

The present invention has been made in view of the above circumstances, and it is an object of the present invention to provide a pad for electrodes which not only is free from the risk of short circuit even when used in an apparatus such as a compact biometric sensor in which electrodes are positioned adjacent to each other, but also is easy to handle, and which allows stable measurement and is unlikely to cause stuffiness or rashes.

Solution to Problem

As a result of intensive research, the present inventors have found that the aforementioned problems can be solved by the following pad for electrodes.

That is, the pad for electrodes of the present invention has the following configuration.

[1] A pad for electrodes including: a first conductive adhesive sheet for connection with an electrode; a second conductive adhesive sheet for connection with another electrode, the second conductive adhesive sheet positioned to be spaced apart from the first conductive adhesive sheet in a planar direction of each conductive adhesive sheet; and a base supporting the first conductive adhesive sheet and the second conductive adhesive sheet, the base overlapping a part of the first conductive adhesive sheet and a part of the second conductive adhesive sheet, at least one surface of each of the first conductive adhesive sheet and the second conductive adhesive sheet being exposed, each of the first conductive adhesive sheet and the second conductive adhesive sheet having a thickness compressibility of 10% or less and a thickness recovery ratio of 95% or more as measured by respective measurement methods below, the base being a non-electroconductive material having a water absorption capacity of 1 to 1.5 times as measured by a measurement method below, and the pad having a moisture permeability of 1,000 $g/m^2/24$ h or more as measured with respect to a region where the base overlaps a part of the first conductive adhesive sheet and a part of the second conductive adhesive sheet.

[Method for Measuring Thickness Compressibility]

A conductive adhesive sheet of 20 mm×20 mm is used as a measurement sample and a thickness thereof is measured (initial sheet thickness). A weight of 5 kg with a bottom surface of 90 mm×140 mm is placed on the measurement sample for 10 seconds, the weight is then immediately removed from the measurement sample, and the thickness of the measurement sample is measured (compressed sheet thickness). The thickness compressibility is obtained from equation (1) below.

$$\text{Thickness compressibility (\%)} = 100 \times (\text{initial sheet thickness} - \text{compressed sheet thickness})/\text{initial sheet thickness} \quad (1)$$

[Method for Measuring Thickness Recovery Ratio]

In the method for measuring the thickness compressibility, after the 5 kg weight is removed and then left for 5 minutes, the thickness of the measurement sample is immediately measured (recovered sheet thickness). The thickness recovery ratio is obtained from equation (2) below.

$$\text{Thickness recovery ratio (\%)} = 100 \times \text{Recovered Sheet Thickness}/\text{Initial Sheet Thickness} \quad (2)$$

[Method for Measuring Water Absorption Capacity]

A base of 50 mm×50 mm is used as a measurement sample and a mass thereof is measured (mass of base before immersion). The measurement sample is immersed in water at 20° C. and the mass after 24 hours from immersion is measured (mass of base after immersion). The water absorption capacity is obtained from equation (3) below.

Water absorption capacity (times)=mass of base after immersion/mass of base before immersion (3)

[2] The pad for electrodes according to [1], in which each of the first conductive adhesive sheet and the second conductive adhesive sheet has both surfaces thereof exposed.

[3] The pad for electrodes according to [1] or [2], in which one or both of the first conductive adhesive sheet and the second conductive adhesive sheet is an acrylamide-based hydrogel.

[4] The pad for electrodes according to any one of [1] to [3], in which the base is a woven fabric or a nonwoven fabric.

[5] The pad for electrodes according to any one of [1] to [4], which is used for a biometric sensor. [6] The pad for electrodes according to any one of [1] to [4], which is used for an industrial sensor.

Advantageous Effects of Invention

The pad for electrodes of the present invention not only is free from the risk of causing a short circuit between the electrodes even when used in an apparatus such as a compact biometric sensor, but also has excellent user-friendliness due to its easy handling, and the pad further allows stable measurement and is unlikely to cause stuffiness or rashes.

DESCRIPTION OF EMBODIMENTS

Description will be given below of an embodiment of the pad for electrodes of the present invention with reference to the drawings.

<Pad for Electrodes>

Figure 1:
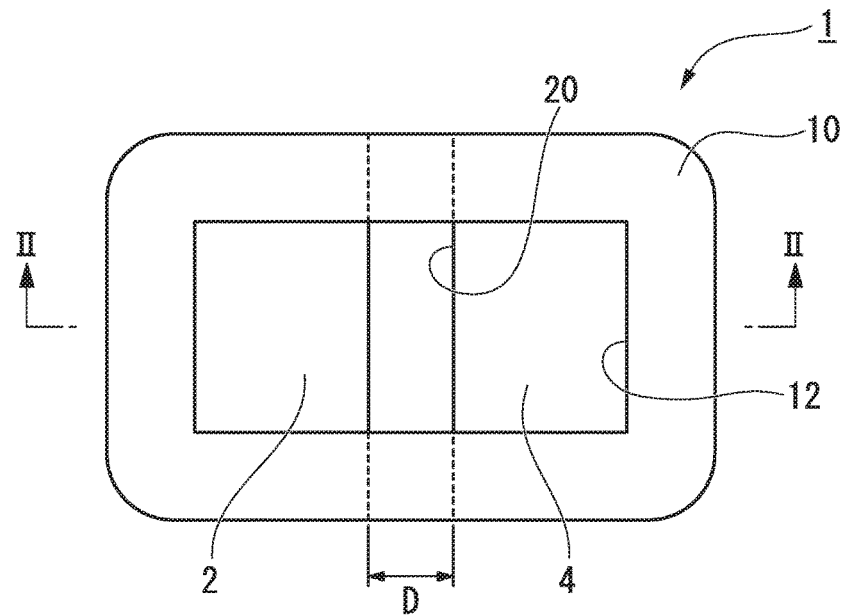
FIG. 1 is a plan view of a pad for electrodes of the present invention.
Figure 2:
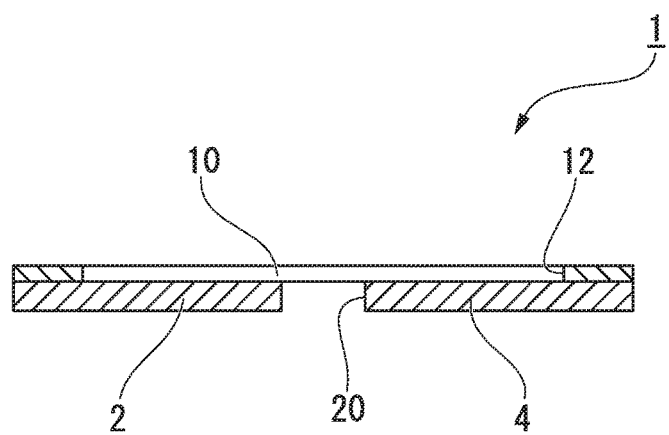
FIG. 2 is a cross-sectional view taken along line II-II of FIG. 1.

The pad 1 for electrodes of FIG. 1 and FIG. 2 is provided with a first conductive adhesive sheet 2, a second conductive adhesive sheet 4, and a base 10 which is laminated on the first conductive adhesive sheet 2 and the second conductive adhesive sheet 4 and which supports the first conductive adhesive sheet 2 and the second conductive adhesive sheet 4.

The first conductive adhesive sheet 2 and the second conductive adhesive sheet 4 are attached to one surface of the base 10.

The pad 1 for electrodes is substantially rectangular in plan view with its sides longer in one direction. The "substantially rectangular" shape is a concept encompassing shapes in which some or all of the four corners are cut away with a curved or a straight line and shapes in which one or more of the four sides are curved.

The size of the pad 1 for electrodes is not particularly limited, but, for example, the long side is 50 to 110 mm and the short side is 30 to 70 mm.

The thickness of the pad 1 for electrodes is not particularly limited, but is, for example, 0.5 to 2.0 mm. If the thickness is less than the above lower limit value, the pad 1 for electrodes becomes too soft and may ruin the easy handling of the pad 1". If the thickness exceeds the above upper limit value, the flexibility of the pad 1 for electrodes may be impaired, resulting in poor handling of the pad 1.

The base 10 is in the form of a flat plate having a substantially rectangular shape in plan view, with its sides longer in one direction.

An opening 12 having a substantially rectangular shape in a plan view is formed on the base 10 so that the base 10 has a frame shape.

The first conductive adhesive sheet 2 is of a flat plate shape having a substantially rectangular shape in a plan view, and the plan view area thereof is smaller than the plan view area of the base 10. The first conductive adhesive sheet 2 is provided so as to cover a part of the opening 12 of the base 10, and three sides of the first conductive adhesive sheet 2 overlap one short side of the base 10 and the two sides adjacent to this short side. In plan view, a part of the first conductive adhesive sheet 2 is exposed through the opening 12, and in the bottom view, the entire first conductive adhesive sheet 2 is exposed. That is, both surfaces of the first conductive adhesive sheet 2 are exposed.

The second conductive adhesive sheet 4 has the same shape as the first conductive adhesive sheet 2. The second conductive adhesive sheet 4 is positioned to be spaced apart from the first conductive adhesive sheet 2 in the longitudinal direction of the base 10 and is provided so as to cover a part of the opening 12. That is, the first conductive adhesive sheet 2 and the second conductive adhesive sheet 4 are separated in the planar direction of the first conductive adhesive sheet 2.

In the present embodiment, the three sides of the second conductive adhesive sheet 4 overlap the side forming the other short side of the base 10 and the two sides adjacent to this short side. In plan view, a part of the second conductive adhesive sheet 4 is exposed through the opening 12, and in the bottom view, the entire second conductive adhesive sheet 4 is exposed. That is, both surfaces of the second conductive adhesive sheet 4 are exposed.

A window 20 penetrating the pad 1 for electrodes in the thickness direction is formed between the first conductive adhesive sheet 2 and the second conductive adhesive sheet 4. The window 20 is a rectangle having a short side in the direction of separation between the first conductive adhesive sheet 2 and the second conductive adhesive sheet 4 in plan view.

A separation distance D between the first conductive adhesive sheet 2 and the second conductive adhesive sheet 4 is set to a distance such that the electrodes connected to the first and second conductive adhesive sheets are not short-circuited, for example, 5 to 20 mm.

In the pad 1 for electrodes, the moisture permeability of a U-shaped region formed by overlap between a part of the first conductive adhesive sheet 2 and the base 10 is 1,000 g/m$^2$/24 h or more, preferably 2,000 g/m$^2$/24 h or more, and more preferably 3,000 g/m$^2$/24 h or more.

When the moisture permeability is less than 1,000 g/m$^2$ 24 h, the stuffiness and rashes cannot be sufficiently suppressed. The moisture permeability is easily adjusted by, for example, adjusting the thickness or the mass per unit area of the first conductive adhesive sheet 2, or by adjusting the moisture permeability of the base 10.

The moisture permeability of the U-shaped region formed by overlap between a part of the second conductive adhesive sheet 4 and the base 10 is the same as the moisture permeability of the region formed by laminating the first conductive adhesive sheet 2 and the base 10.

In the present invention, the moisture permeability of a region where a part of the first conductive adhesive sheet 2 and the base 10 overlap is measured as follows.

[Method for Measuring Moisture Permeability]

The moisture permeability in the present invention is a value measured according to the moisture permeability test method of JIS Z 0208: 1976. Specifically, the moisture permeability is measured by the following procedure.

A laminate in which the first conductive adhesive sheet 2 and the base 10 are overlapped is prepared and cut into a test piece of φ70 mm.

15 g of anhydrous calcium chloride is put into a moisture permeable cup (JIS standard item φ60 mm), the opening of the moisture permeable cup is covered with the test piece (the first conductive adhesive sheet side of the test piece comes into contact with the opening), the moisture permeable cup is sealed by applying dissolved paraffin on the adhesive surface of the first conductive adhesive sheet of the test piece. The sealed moisture permeable cup is allowed to stand for 24 hours in an environment of 40±0.5° C. and 90±2% relative humidity such that the sealed side faces upward, and the mass of the sealed moisture permeable cup is weighed. Then, moisture permeability is calculated by the following equation.

Moisture permeability $(g/m^2/24\ h) = u/s$

Here, s is the moisture permeation area $(m^2)$, and u is the total (g) of the absolute values of the increased masses.

The method for measuring the moisture permeability of the region where a part of the second conductive adhesive sheet 4 and the base 10 overlap is the same as the method for measuring the moisture permeability of a region where a part of the first conductive adhesive sheet 2 and the base 10 overlap.

<Conductive Adhesive Sheet>

The first conductive adhesive sheet 2 has a thickness compressibility of 10% or less and a thickness recovery ratio of 95% or more. In addition, as the first conductive adhesive sheet 2, normally, a sheet is used which has such a conductivity that allows an electric signal to be conducted from the object to be measured and has such an adhesiveness that allows the adhesive sheet to be attached to the electrode and the object to be measured.

The first conductive adhesive sheet 2 satisfying the above requirements can be obtained as follows.

The first conductive adhesive sheet 2 is formed of a gel such as a hydrogel or an organogel, and the first conductive adhesive sheet 2 is preferably formed of a hydrogel from the point of view of excellent biocompatibility.

Examples of hydrogels include a conductive polymer hydrogel including a wetting agent, an electrolyte salt and water in a polymer matrix obtained by copolymerizing a polymerizable monomer and a cross-linkable monomer.

Examples of polymerizable monomers include (meth)acrylic acid, maleic acid, fumaric acid, itaconic acid, crotonic acid, vinyl sulfonic acid, allyl sulfonic acid, salts thereof, and the like. In addition to these monomers, further examples include acrylic acid esters such as (poly)ethylene glycol (meth)acrylate, (poly)propylene glycol (meth)acrylate, and (poly)glycerin (meth)acrylate, N-substituted (meth)acrylamides such as (meth)acrylamide, N-methyl (meth)acrylamide, N-ethyl (meth)acrylamide, N-propyl (meth)acrylamide, N-butyl (meth)acrylamide, N,N-dimethyl (meth)acrylamide, N-methylol acrylamide, and diacetone acrylamide, N-vinyl amide derivatives such as N-vinyl pyrrolidone, N-vinyl formamide, N-vinyl acetamide, and the like. Any of these polymerizable monomers may be used alone as one type, or two or more types may be used in combination. In the examples described above, (meth)acrylic means acrylic or methacrylic.

Among these polymerizable monomers, a non-ionic polymerizable monomer is preferable from the viewpoint of improving water resistance. In particular, the non-ionic polymerizable monomer preferably has a pH of 4 to 9 as a 1 mass % aqueous solution of the monomer in the form of a free acid or base, and the non-ionic polymerizable monomer more preferably has a pH of 6 to 8. Examples of such polymerizable monomers include acrylate esters such as (poly)ethylene glycol (meth)acrylate, (poly)propylene glycol (meth)acrylate, (poly)glycerin (meth)acrylate, N-substituted (meth)acrylamides such as (meth)acrylamide, N-methyl (meth)acrylamide, N-ethyl (meth)acrylamide, N-propyl (meth)acrylamide, N-butyl (meth)acrylamide, N,N-dimethyl (meth)acrylamide, N-methylol acrylamide, and diacetone acrylamide, N-vinyl amide derivatives such as N-vinyl pyrrolidone, N-vinyl formamide, N-vinyl acetamide, and the like. Any of these polymerizable monomers may be used alone as one type, or two or more types may be used in combination.

Here, in a polymer matrix produced using an ionic polymerizable monomer, ionic groups in the side chains in the polymer hydrogel are ionized, and the polymer matrix is set to a state charged to either positive or negative. For this reason, the linear chains of the polymer matrix have a property of always repelling each other, and when a large amount of water comes into contact with the polymer matrix, the network of the polymer matrix opens for a short time and exhibits a greater water absorption capacity. On the other hand, if non-ionic polymerizable monomers are used, such changes are small. In addition, in the absence of ionic groups in the polymer matrix, the polymer matrix is not affected by electricity when performing electrical measurements or treatments. Therefore, the electrical repulsion is unlikely to occur at the interface between the electrode element or the like and the polymer hydrogel, and the gel shrinkage due to the addition of the electrolyte for imparting conductivity is unlikely to occur as well. Therefore, when a non-ionic polymer monomer is used, it is possible to obtain a higher performance electroconductive polymer hydrogel. In addition, there is another advantage that the use of additive is easy in the case of producing a polymer hydrogel including a medicinal component and various additives, because even in such a case where the medicinal component or the like is an electrolyte, no interaction occurs between an ionic group in the polymerizable monomer and a drug or the like.

Furthermore, as a non-ionic polymerizable monomer, it is preferable to use a nonionic polymerizable monomer having a ratio of hydrophobic parts to hydrophilic parts [(molecular weight−sum of atomic weights of hydrophilic parts)/sum of atomic weights of hydrophilic parts] of 0.8 to 2.0. Here, the hydrophilic parts mean the smallest unit exhibiting hydrophilicity (for example, a hydroxyl group (—OH), an ether group (—O—), a carbonyl group (—C(=O)—), and the like) and the hydrophobic parts mean the other parts. By using such a non-ionic polymerizable monomer in an amount of 25 mass % or more in the polymerizable monomer, the hydrophobic parts are present in a well-balanced state in the polymer matrix such that the electrostatic interaction with the hydrophobic parts of the wetting agent is increased, whereby it becomes possible to further reduce the elution of the wetting agent from inside of the electroconductive polymer hydrogel. Furthermore, in the case where a polymer obtained by polymerizing a polyvalent alcohol monomer is blended as a wetting agent, it is possible to further reduce the elution of the wetting agent from inside of the gel due to the electrostatic interaction between the hydrophobic parts of the polymer matrix and the hydrophobic parts of the wetting agent.

The term "polymer matrix" as used herein refers to a matrix obtained by polymerization cross-linking of a polymerizable monomer and a cross-linkable monomer.

The amount of the polymerizable monomer is preferably 90 to 99.95 mass % with respect to the total amount of the polymer matrix. When the amount is less than 90 mass %, the polymerizable monomer may become a hard and brittle gel. When the amount exceeds 99.95 mass %, the cross-linking density is low, which may results not only in poor dimensional stability, but also in larger interval of the cross-linking of the network, which increases the expansion of the network at the time of water absorption, and thereby increases the water absorption capacity.

As the cross-linkable monomer, it is preferable to use a monomer having two or more polymerizable double bonds in the molecule. Examples of cross-linkable monomers include polyfunctional (meth)acrylamides or (meth)acrylates such as methylene bis(meth)acrylamide, ethylene bis (meth)acrylamide, (poly)ethylene glycol di(meth)acrylate, (poly)propylene glycol di(meth)acrylate, glycerin di(meth) acrylate, and glycerin tri(meth)acrylate, tetraallyloxyethane, diallylammonium chloride, and the like. Any of these cross-linkable monomers may be used alone as one type, or two or more types may be used in combination. Since a small amount of cross-linkable monomer may be used relative to the non-ionic polymerizable monomer, it is possible to use either ionic or non-ionic monomers, but non-ionic monomers are preferable. Here, as the cross-linkable monomer having two or more polymerizable double bonds in the molecule, it is also possible to use a polyglycerin derivative which is a polyfunctional compound having two or more (meth)acryloyl groups or vinyl groups described in Japanese Patent No. 2803886 and having a molecular weight of 400 or more.

The amount of the cross-linkable monomer is preferably 0.05 to 10 mass % with respect to the total amount of the polymer matrix. When the amount is less than 0.05 mass %, the cross-linking density is low, which may results not only in poor dimensional stability, but also in larger interval of the cross-linking of the network, which increases the expansion of the network at the time of water absorption, and thereby increases the water absorption capacity. When the amount exceeds 10 mass %, the cross-linkable monomer may become a hard and brittle gel.

Furthermore, the total amount of the cross-linkable monomer is preferably 5 mass % or less of the entire conductive polymer hydrogel.

The concentration of the polymer matrix included in the conductive polymer hydrogel is preferably 5 to 50 mass %, and more preferably 5 to 40 mass %. With respect to this concentration of the polymer matrix in the gel, the concentration of less than 5 mass % is too low to completely hold the solvent, so that the bleeding is likely to occur, and the gel may have weak stiffness. On the other hand, when the concentration exceeds 50 mass %, the heat generation during polymerization becomes too large, so that the solvent boils and air bubbles are mixed into the gel, which may makes it difficult to obtain a satisfactory gel.

Examples of the wetting agent include polyvalent alcohol monomers, polymers obtained by polymerizing polyvalent alcohol monomers, and mixtures thereof.

The wetting agent is preferably, for example, a wetting agent including 50 mass % or more of a polymer obtained by polymerizing a polyvalent alcohol monomer and including a tri- or higher valent polyvalent alcohol monomer as a polyvalent alcohol monomer. Further, it is preferred that the average molecular weight of the polymer is 150 to 4,000, and the wetting agent exhibits water-solubility and satisfies the following condition: ((number of ether groups present in the polymer+number of hydroxyl groups present in the polymer)/number of carbon atoms present in the polymer) ≥⅓.

The average molecular weight of the polymer obtained by polymerizing the polyvalent alcohol monomer is preferably 150 to 4,000, and more preferably 300 to 4,000. The average molecular weight means a number average molecular weight measured by gel permeation chromatography (GPC).

In addition, the polymer obtained by polymerizing the polyvalent alcohol monomer is water-soluble. The phrase "water-soluble" means that at least 10 g of the polymer is dissolved in 100 g of water at 25° C. Furthermore, as a polymer obtained by polymerizing a polyvalent alcohol monomer, it is preferable to use a polymer which satisfies the following condition: ((number of ether groups present in the polymer+number of hydroxyl groups present in the polymer)/number of carbon atoms present in the polymer) ≥⅓. In addition, units derived from tri- or higher valent polyvalent alcohol monomers being disposed in the repeating unit of the polymer improve the wetting function as a wetting agent, increase electrostatic interaction with the polymer matrix and solvent, and make it possible to further reduce the elution of the wetting agent from the inside of the gel.

Polymers obtained by polymerizing polyvalent alcohol monomers include water-soluble polymers obtained by polymerizing one or two or more types of monomers such as ethylene glycol, propylene glycol, butanediol, pentanediol, glycerin, pentaerythritol, sorbitol, sorbitan, and saccharides. From the viewpoint of the viscoelastic properties of the conductive polymer hydrogel and the handling at the time of production, the polymer is preferably liquid at room temperature.

The polymer obtained by polymerizing the polyvalent alcohol monomer is preferably a polymer obtained by polymerizing a polyvalent alcohol monomer including a tri- or higher valent polyvalent alcohol monomer. Examples of such a polymer include polymers obtained by polymerizing a polyvalent alcohol monomer including at least a tri- or higher valent polyvalent alcohol such as glycerin, pentaerythritol, sorbitol, sorbitan, or saccharides. The tri- or higher valent polyvalent alcohol monomer is preferably included in the polymer in an amount of 50 to 100 mass %. Unreacted hydroxyl groups may remain in the tri- or higher valent polyvalent alcohol monomer unit. When units derived from a trivalent or higher polyvalent alcohol monomer are present, unreacted hydroxyl groups may remain in the polymer, which can improve the wetting performance.

The polymer obtained by polymerizing a polyvalent alcohol monomer including a tri- or hither valent polyvalent alcohol monomer is also preferably in a liquid state at room temperature. For example, polyglycerin obtained by homopolymerizing glycerin which is liquid at room temperature is also liquid at room temperature; therefore, polyglycerin also excels in handling. In addition, monomers which are solid at room temperature such as sorbitol and saccharides may be liquefied by copolymerization with other types of monomers, or grafting with a liquid polymer such as polyglycerin.

The amount of the wetting agent in the conductive polymer hydrogel is preferably 10 to 80 mass %, and more preferably 20 to 70 mass %. The amount of less than 10 mass % may result in poor wettability of the gel and vigorous evaporation of water vapor, which decreases not only stability of the gel over time but also flexibility of the gel, whereby the adhesiveness may become insufficient. When the amount exceeds 80 mass %, the viscosity becomes excessively high at the time of preparing a monomer mixture including a polymerizable monomer, a cross-linkable monomer, a wetting agent, and water, so that the handling deteriorates, and bubbles are caused to be mixed in when producing the conductive polymer hydrogel.

Examples of the electrolyte salt described above include alkali metal halides or alkaline earth metal halides such as sodium halide, potassium halide, magnesium halide, and calcium halide, other metal halides, hypochlorites of each type of metal, inorganic salts such as chlorite, chlorate, perchlorate, sulfate, nitrate, phosphate, ammonium salt, and complex salts of each type, monovalent organic carboxylic acid salts such as acetic acid, benzoic acid, and lactic acid, monovalent or di- or higher valent salts of polycarboxylic acids such as phthalic acid, succinic acid, adipic acid, citric acid, and tartaric acid, organic acid metal salts or organic ammonium salts such as sulfonic acid and amino acids, polymer electrolyte salts such as poly(meth)acrylic acid, polyvinyl sulfonic acid, polytert-butylacrylamide sulfonic acid, polyallylamine, and polyethyleneimine, and the like. In addition, it is also possible to use silicates, aluminates, metal oxides, hydroxides, and the like.

The amount of the electrolyte salt in the conductive polymer hydrogel is preferably 13 mass % or less, and more preferably 10 mass % or less. When the amount exceeds 13 mass %, dissolution of the salt becomes difficult, so that precipitation of crystals may occur inside the gel, and dissolution of other components may be inhibited. In addition, no further improvement in electroconductivity is available even when the electrolyte salt is added in an amount exceeding 13 mass %, which is not preferable from the viewpoint of cost.

In addition, the water content of the conductive polymer hydrogel is preferably 5 to 50 mass %, and more preferably 5 to 40 mass %. When the content is less than 5 mass %, the water vapor content of the gel is small relative to the equilibrium water vapor content of the gel, so that the water vapor absorption may become excessively high. When the content exceeds 50 mass %, the difference from the equilibrium water vapor content of the gel is large, so that the gel may shrink due to drying or may undergo large changes in the physical properties.

Among the above conductive polymer hydrogels, as a polymerizable monomer, acrylamide-based hydrogels obtained by using (meth)acrylamide, N-substituted (meth)acrylamide, N-vinylamide derivatives, and the like are preferable.

An acrylamide-based hydrogel is a base excellent in biocompatibility and corrosion resistance. In addition, the polymerizable monomers described above are excellent in reactivity, so that the amount of residual monomers in the gel is small and skin irritation is also suppressed.

As the material of the second conductive adhesive sheet 4, the same material as mentioned for the first conductive adhesive sheet 2 can be used. Here, the material of the second conductive adhesive sheet 4 may be the same as or different from the material of the first conductive adhesive sheet 2.

The thickness of the first conductive adhesive sheet 2 is not particularly limited but is, for example, 0.3 to 1.2 mm. When the thickness is less than 0.3 mm, the sheet may become soft and weak. When the thickness exceeds 1.2 mm, the sheet becomes too thick, so that the pad 1 for electrodes is not available in a compact size, whereby the handling may be impaired.

Regarding the thickness of the second conductive adhesive sheet 4, the same applies as described above for the thickness of the first conductive adhesive sheet 2.

The thickness of the first conductive adhesive sheet 2 and the thickness of the second conductive adhesive sheet 4 may be the same or different.

The adhesive strength of the first conductive adhesive sheet 2 is not particularly limited but is, for example, 550 to 1,350 g/20 mm. When the adhesive strength is less than 550 g/20 mm, the adhesion of the sheet to the electrode and the object to be measured may be impaired. On the other hand, when the adhesive strength exceeds 1,350 g/20 mm, it becomes difficult to peel off the sheet from the electrode and the object to be measured, and extra force may be required for peeling off the sheet, which may deform the sheet. In addition, the risk of skin irritation at the time of peeling off may increase as well.

Here, in this "adhesive strength" test method, the first conductive adhesive sheet 2 is cut into a piece of 20 mm×100 mm and used as a measurement sample, the measurement sample is attached to a Bakelite plate, and the adhesive strength is measured in accordance with JIS Z 0237 immediately after having been kept under conditions of 23° C. and 50% RH for 30 minutes.

Regarding the adhesive strength of the second conductive adhesive sheet 4, the same applies as described above for the adhesive strength of the first conductive adhesive sheet 2. The adhesive strength of the first conductive adhesive sheet 2 and the adhesive strength of the second conductive adhesive sheet 4 may be the same or different.

The first conductive adhesive sheet 2 has a thickness compressibility of 10% or less as measured by the following measurement method.

[Method for Measuring Thickness Compressibility]

A measurement sample (hereinafter also referred to as the "initial sheet") in which the first conductive adhesive sheet is set to 20 mm×20 mm by cutting or the like is prepared. The thickness of the initial sheet is measured as the "initial sheet thickness". Next, a weight of 5 kg with a bottom surface of 90 mm×140 mm is placed on the initial sheet, the sheet is left for 10 seconds, and the weight is then immediately removed to prepare the sheet (hereinafter also referred to as the "compressed sheet"). The thickness of the compressed sheet is measured as the "compressed sheet thickness". Then, the thickness compressibility is obtained from the following equation (1).

$$\text{Thickness compressibility (\%)} = 100 \times (\text{initial sheet thickness} - \text{compressed sheet thickness})/\text{initial sheet thickness} \quad (1)$$

The thickness compressibility of the first conductive adhesive sheet 2 is preferably 7.5% or less, and more preferably 6.5% or less.

When the thickness compressibility of the first conductive adhesive sheet 2 exceeds 10%, the first conductive adhesive sheet 2 is likely to be deformed. This causes the fluctuation of resistance of the pad for electrodes, which prevents accurate transmission of electric signals from the object to be measured to the electrode, and thereby prevents stable measurement.

Regarding the method for measuring the thickness compressibility of the second conductive adhesive sheet 4, the same applies as described above for the method for measuring the thickness compressibility of the first conductive adhesive sheet 2.

Regarding the thickness compressibility of the second conductive adhesive sheet 4, the same applies as described above for the thickness compressibility of the first conductive adhesive sheet 2. The thickness compressibility of the first conductive adhesive sheet 2 and the thickness compressibility of the second conductive adhesive sheet 4 may be the same or different.

The first conductive adhesive sheet 2 has a thickness recovery ratio of 95% or more as measured by the following measurement method.

[Method for Measuring Thickness Recovery Ratio]

In the method for measuring the thickness compressibility, a measurement sample (hereinafter also referred to as the "recovered sheet") left for 5 minutes after removing a weight of 5 kg is prepared. The thickness of the recovered sheet is measured as the "recovered sheet thickness". Then, the thickness recovery ratio is obtained from the following equation (2).

$$\text{Thickness recovery ratio (\%)} = 100 \times \text{Recovered Sheet Thickness/Initial Sheet Thickness} \quad (2)$$

The thickness recovery ratio of the first conductive adhesive sheet 2 is preferably 96% or more, and more preferably 98% or more.

When the thickness recovery ratio of the first conductive adhesive sheet 2 is less than 95%, the shape retention of the first conductive adhesive sheet 2 deteriorates, and the degree of deformation of the first conductive adhesive sheet 2 increases over time. This causes a large fluctuation of resistance of the first conductive adhesive sheet 2, which prevents stable measurement.

Regarding the method for measuring the thickness recovery ratio of the second conductive adhesive sheet 4, the same applies as described above for the method for measuring the thickness recovery ratio of the first conductive adhesive sheet 2.

Regarding the thickness recovery ratio of the second conductive adhesive sheet 4, the same applies as described above for the thickness recovery ratio of the first conductive adhesive sheet 2. The thickness recovery ratio of the first conductive adhesive sheet 2 and the thickness recovery ratio of the second conductive adhesive sheet 4 may be the same or different.

Each of the measurements of the thickness compressibility and thickness recovery ratio is performed in the air (for example, at a temperature of 20 to 27° C. and a relative humidity of 40 to 60%). In addition, the measurement of the thicknesses of the initial sheet, the compressed sheet and the recovered sheet is performed using a thickness gauge ("Thickness Gauge" manufactured by Mitutoyo Corporation) with the minimum measurable thickness of 1/100 mm.

Further, the first conductive adhesive sheet 2 may be provided with an intermediate base in the layers thereof. Providing the intermediate base increases the strength of the first conductive adhesive sheet 2, thereby improving the handling and workability of the sheet, and also enables the pad 1 for electrodes to be handled integrally with more ease. As the intermediate layer, a material having a high opening ratio is preferable, for example, a material made of a woven fabric or a nonwoven fabric such as nylon, or polyester is preferable.

It is also possible to provide an intermediate base similar to the first conductive adhesive sheet 2 on the second conductive adhesive sheet 4. The intermediate base of the first conductive adhesive sheet 2 and the intermediate base of the second conductive adhesive sheet 4 may be the same or different. In addition, the intermediate base may be provided only on one or both of the first conductive adhesive sheet 2 or the second conductive adhesive sheet 4.

The first conductive adhesive sheet 2 can be produced, for example, as follows.

A blend solution is prepared by mixing the polymerizable monomer, a cross-linkable monomer, a wetting agent, an electrolyte salt, and water, followed by addition of a photopolymerization initiator. Next, the above blend solution is spread on a film such as a polyethylene terephthalate film or the like at an arbitrary thickness and irradiated with ultraviolet rays to cause a polymerization cross-linking reaction to form a sheet-like gel. The obtained sheet-like gel is cut into a desired shape to obtain the first conductive adhesive sheet 2.

Here, as necessary, after spreading the blend solution described above on the film at an arbitrary thickness, the sheet-like gel provided with an intermediate base may be obtained by arranging the intermediate base described above in the layer of the spread blend solution and irradiating the intermediate base with UV irradiation to cause a polymerization cross-linking reaction. The resultant is cut into a desired shape to obtain the first conductive adhesive sheet 2 provided with the intermediate base.

The method for manufacturing the second conductive adhesive sheet 4 is the same as in the case of the first conductive adhesive sheet 2.

<Base 10>

The base 10 in the present invention is a non-conductive base having a water absorption capacity of 1 to 1.5 times.

The water absorption capacity of the base of the present invention is a value measured by the following measurement method.

[Method for Measuring Water Absorption Capacity]

A measurement sample is prepared by resizing a base into 50 mm×50 mm by cutting or the like, followed by storing in a thermo-hygrostat chamber at 23° C. and a relative humidity of 50% RH for 24 hours (hereinafter also referred to as "base before immersion"). The base before immersion is taken out from the thermo-hygrostat chamber, the mass thereof is measured immediately as the "mass of base before immersion". Thereafter, the base before immersion is immersed in water (ion-exchanged water) at 20° C. for 24 hours, taken out from the water after immersion, and water droplets attached to the surface are lightly wiped with gauze (hereinafter also referred to as "base after immersion") to produce a measurement sample. The mass of the base after immersion is measured as the "mass of base after immersion". Then, the water absorption capacity of the base is obtained from equation (3) below.

$$\text{Water absorption capacity (times)} = \text{mass of base after immersion/mass of base before immersion} \quad (3)$$

When the water absorption capacity of the base 10 is more than 1.5 times, water vapor such as sweat is easily absorbed in the base 10, which may lower the resistance of the base 10 to prevent stable measurement, and may cause a short circuit between the electrodes connected with the first conductive adhesive sheet and the second conductive adhesive sheet. The water absorption capacity of the base 10 is preferably 1.3 times or less, more preferably 1.2 times or less, and even more preferably 1.1 times or less.

In the present invention, the non-conductive base refers to a base which is in a state where the resistance is too high such that resistance cannot be measured by the following measurement method for both of the base before immersion and the base after immersion (i.e., in an insulated state).

[Method for Measuring Resistance]

The electric resistance is measured for each of the base before immersion and the base after immersion as described in the [Method for Measuring Water Absorption Capacity] described above. The measurement of the electric resistance is carried out using a Digital Multimeter CD 771 apparatus manufactured by Sanwa Electric Instrument Co., Ltd., by placing two leads of the apparatus on the surfaces of each of the base before immersion and the base after immersion such that the distance between the tips is 20 mm. The measurement of electrical resistance is performed in the air (for example, at a temperature of 20 to 27° C. and a relative humidity of 40 to 60%).

Examples of the base 10 include films, sheets, woven fabrics, nonwoven fabrics and the like produced from known non-conductive materials such as polyolefins (such as polyester, polyethylene, and polypropylene), pulp, rayon, and nylon.

Among the above, woven fabrics or nonwoven fabrics are preferable since these are excellent in processability, moisture permeability and adhesion to a conductive adhesive sheet. Among these, polyolefin nonwoven fabrics produced by the spun bond method are particularly preferable.

The thickness of the base 10 is not particularly limited, but is, for example, 0.2 to 1.2 mm. When the thickness is less than 0.2 mm, the base 10 becomes soft and weak, which may impair the shape retention of the pad 1 for electrodes. When the thickness exceeds 1.2 mm, the base 10 becomes too thick so that the pad 1 for electrodes is not available in a compact size, whereby the handling may be impaired.

The grammage of the base 10 is not particularly limited, but is, for example, 50 to 110 g/m$^2$. When the grammage is less than 50 g/m$^2$, the base 10 becomes soft and weak, which may impair the shape retention of the pad 1 for electrodes. When the grammage exceeds 110 g/m$^2$, the flexibility of the base 10 is impaired, and the handling of the pad 1 for electrodes may be impaired.

<Method for Producing Pad for Electrodes>

Figure 3:
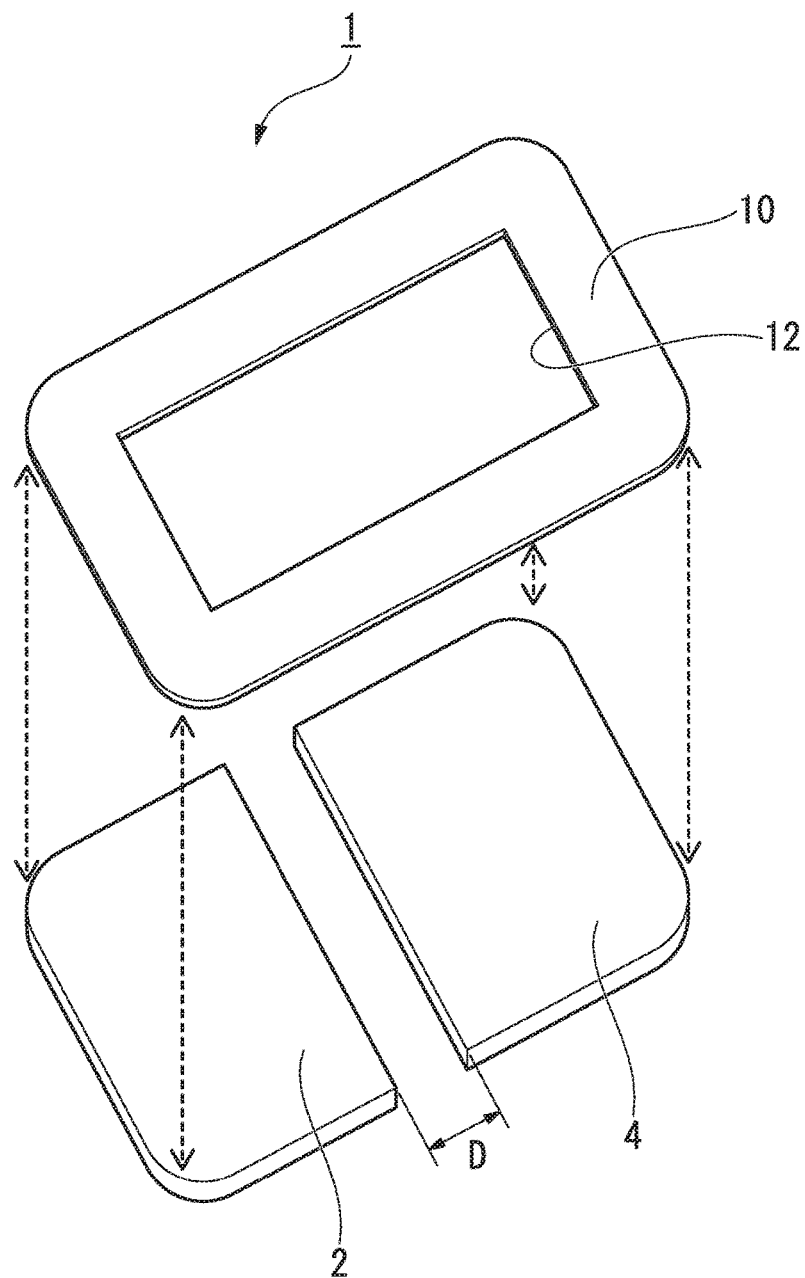
FIG. 3 is a perspective view of a pad for electrodes of the present invention.

The method for producing the pad for electrodes of the present invention is not particularly limited. An example of a method for producing the pad 1 for electrodes will be described with reference to FIG. 3.

First, the first conductive adhesive sheet 2 and the second conductive adhesive sheet 4 produced as described above are arranged on the same plane with a desired distance D between the sheets. Thereafter, the base 10 processed in advance into a frame shape is arranged so as to face the first conductive adhesive sheet 2 and the second conductive adhesive sheet 4. Then, the pad 1 for electrodes can be easily produced by bonding the base 10 to the first conductive adhesive sheet 2 and the second conductive adhesive sheet 4 so as to integrate these components.

Here, as necessary, the first conductive adhesive sheet 2 and the second conductive adhesive sheet 4 may be coated with an adhesive on their respective surfaces to be bonded with the base 10.

<Use Method>

Hereinbelow, descriptions will be given with respect to a method for using the pad 1 for electrodes by taking a case of using the pad 1 for electrodes as a wearable sensor as an example.

Figure 4:
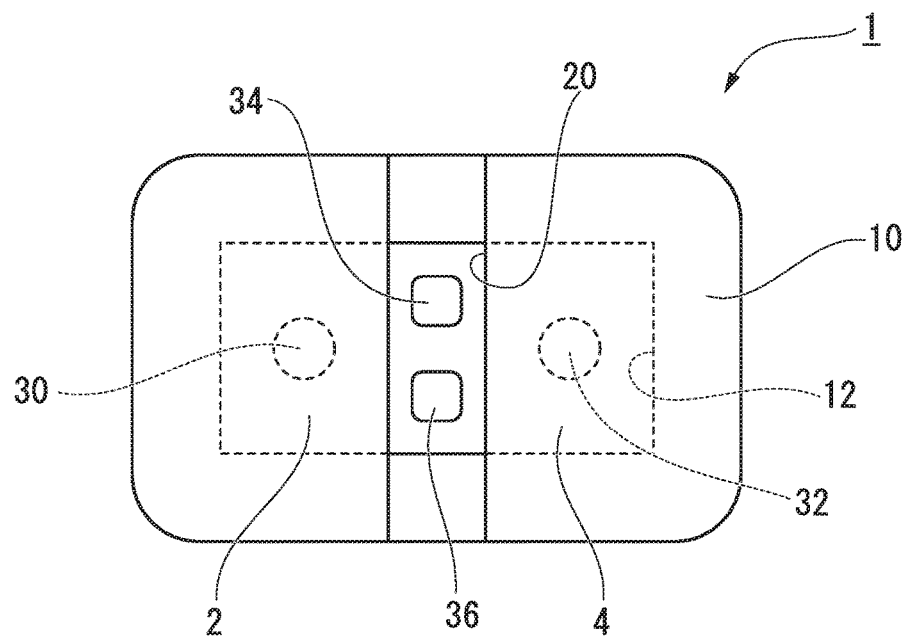
FIG. 4 is a bottom view illustrating a method for using the pad for electrodes of the present invention.

As shown in FIG. 4, in the sensor of the present example, two electrodes 30 and 32 are arranged with an interval therebetween, and an optical sensor 34 and an image sensor 36 are disposed between the two electrodes.

The pad 1 for electrodes and the sensor are arranged to face each other. Here, the surface of the pad 1 for electrodes provided with the base 10, that is, the surface where the first conductive adhesive sheet 2 and the second conductive adhesive sheet 4 are not entirely exposed, and the electrode surface of the sensor are arranged to face each other.

Next, the pad 1 for electrodes is attached to the electrode of the sensor. Here, one electrode 30 of the sensor is attached to the first conductive adhesive sheet 2 exposed through the opening 12 of the pad 1 for electrodes, and the other electrode 32 of the sensor is attached to the second conductive adhesive sheet 4 exposed through the opening 12. In addition, the optical sensor 34 and the image sensor 36 are positioned in the window 20 of the pad 1 for electrodes.

Then, the surface of the pad 1 for electrodes to which the electrode of the sensor is not attached, that is, the surface where the first conductive adhesive sheet 2 and the second conductive adhesive sheet 4 are entirely exposed, and the object to be measured are attached to each other.

Thus, the electrodes 30 and 32 of the sensor and the object to be measured are fixed via the pad 1 for electrodes.

The electrodes 30 and 32 attached to the pad 1 for electrodes detect the electric signals emitted from the object to be measured via the first conductive adhesive sheet 2 and the second conductive adhesive sheet 4 and transmit the signals to the sensor. Here, since the first conductive adhesive sheet 2 and the second conductive adhesive sheet 4 are arranged apart from each other and are supported by the base 10, a short circuit does not occur between the electrodes 30 and 32 connected with the first conductive adhesive sheet 2 and the second conductive adhesive sheet 4.

In addition, since the optical sensor 34 and the image sensor 36 are positioned in the window 20 penetrating the pad 1 for electrodes, it is possible to acquire accurate data without being affected by the conductive adhesive sheets.

<Mechanisms Underlying Effects of the Invention>

In the pad 1 for electrodes described above, the first conductive adhesive sheet 2 and the second conductive adhesive sheet 4 have electrical conductivity, whereby the electrodes 30 and 32 connected to these sheets are able to detect the electric signals emitted from the object to be measured via these sheets.

In addition, in the pad 1 for electrodes, the first conductive adhesive sheet 2 and the second conductive adhesive sheet 4 have adhesiveness, thereby enabling the electrode of the sensor to be favorably fixed to the object to be measured.

In the pad 1 for electrodes, the first conductive adhesive sheet 2 and the second conductive adhesive sheet 4 are arranged apart from each other and supported by the non-conductive base 10. This enables the pad 1 for electrodes to easily prevent a short circuit between the electrode 30 and the electrode 32 which are respectively connected to the first conductive adhesive sheet 2 and the second conductive adhesive sheet 4. In addition, the pad 1 for electrodes can be handled as a single unit, and hence is excellent in handling and user-friendliness.

In the pad 1 for electrodes, the first conductive adhesive sheet 2 and the second conductive adhesive sheet 4 are both exposed through the opening 12 of the base 10, so that electrodes such as wearable biometric sensors can be attached to the exposed sections. Therefore, for example, as shown in FIG. 4, in a case where electrodes of a wearable sensor are attached to the pad 1 for electrodes and the electrodes of the sensor are attached to the object to be measured via the pad 1 for electrodes, it is possible to reliably prevent the electrodes of the sensor from being displaced from the measurement site of the object to be measured or the sensor from falling from the object to be measured.

The first conductive adhesive sheet 2 and the second conductive adhesive sheet 4 have a thickness compressibility of 10% or less. Therefore, deformation of the first conductive adhesive sheet 2 and the second conductive adhesive sheet 4 is suppressed. This results in suppression of fluctuation of the resistance of the pad for electrodes, whereby electric signals can be accurately transmitted from the object to be measured to the electrodes and a stable measurement can be performed.

The first conductive adhesive sheet 2 and the second conductive adhesive sheet 4 have a thickness recovery ratio of 95% or more. Therefore, the first conductive adhesive sheet 2 and the second conductive adhesive sheet 4 are excellent in shape retention and deformation thereof due to aging is suppressed. This enables electric signals to be accurately transmitted from the object to be measured to the electrodes over a long period of time, whereby a stable measurement can be performed.

The base 10 is a non-conductive base having a water absorption capacity of 1 to 1.5 times. Therefore, it is possible to suppress water vapor such as sweat from being absorbed in the base 10 to thereby decrease the resistance of the base 10, and it is also possible to suppress a short circuit of the electrodes connected with the first conductive adhesive sheet 2 and the second conductive adhesive sheet 4.

The pad 1 for electrodes has a moisture permeability of 1,000 $g/m^2/24$ h or more in a region where the first conductive adhesive sheet 2 and the second conductive adhesive sheet 4 are laminated with the base 10. This results in suppression of stuffiness and rashes at the time of attaching the pad 1.

The window 20 penetrating both surfaces is formed in the pad 1 for electrodes, so that it is possible to position a sensor for acquiring data directly from the surface of the object to be measured, such as an optical sensor or an image sensor, in the window 20. Therefore, the pad for electrodes can be suitably used as a pad for electrodes of an apparatus provided with an electrode and a plurality of sensors.

The base 10 has a frame shape whereby the pad 1 for electrodes has favorable shape retention, and the pad 1 for electrodes can be handled as a more integrally formed single unit. Therefore, for example, the pad 1 for electrodes is further improved in handling during an operation of attaching the pad 1 to the object to be measured or an operation of removing the pad 1 from the object.

When one or both of the first conductive adhesive sheet 2 and the second conductive adhesive sheet 4 is formed of a polymer hydrogel, in particular, an acrylamide-based hydrogel, the sheet(s) exhibits further improved adhesion. Further, such a sheet(s) also excels in biocompatibility, and is able to reduce skin irritation. Furthermore, the corrosion resistance is also further improved. Therefore, the pad 1 for electrodes using such a conductive adhesive sheet(s) can be suitably used in a wide range of fields such as biometric sensors and industrial sensors.

Furthermore, the acrylamide-based hydrogel is also excellent in water vapor absorption. For this reason, in a case where the pad 1 for electrodes using such a conductive adhesive sheet(s) is, for example, attached to the skin, the absorption of sweat or the like is excellent and uncomfortable feelings are reduced and a good feel during use is obtained even when the pad 1 for electrodes is used for a long time.

When a woven fabric or a nonwoven fabric is used as the base 10, the flexibility is not impaired and the pad 1 for electrodes follows the surface morphology of the object to be measured and the outer shape of apparatuses such as a biometric sensor more easily. Therefore, even in a case where the surface morphology of the object to be measured or the outer shape of the apparatus has irregularities, the pad 1 for electrodes can follow such surface morphology or outer shape and can be suitably attached to such an object or an apparatus. Furthermore, the woven or nonwoven fabric is excellent in adhesion with the first conductive adhesive sheet 2 and the second conductive adhesive sheet 4; therefore, the integrity of the components of the pad 1 for electrodes is further improved.

In addition, the woven fabric or the nonwoven fabric is excellent in moisture permeability; therefore, the pad 1 for electrodes provided with such fabric on the surface thereof, when for example attached to the skin, exhibits excellent transpiration of sweat or the like, whereby the pad 1 for electrodes can reduce unpleasant feel and give a pleasant feel even when used for a long time.

<Other Embodiments>

The pad for electrodes of the present invention is not limited to the embodiment described above.

In the embodiment described above, the shape of the pad for electrodes is substantially rectangular in plan view, but the shape in plan view is not limited thereto.

For example, the shape may be an arbitrary shape such as an elliptical shape, a perfectly circular shape, a square shape, a diamond shape, a gourd shape, or a penta- or higher polygonal shape.

In the embodiment described above, the shape of the first conductive adhesive sheet is a substantially rectangular shape in plan view, but the shape in plan view is not limited thereto. For example, the shape may be an arbitrary shape such as a substantially semi-circular shape, a perfectly circular shape, an elliptical shape, a square shape, a diamond shape, a gourd shape, or a penta- or higher polygonal shape.

The same applies to the second conductive adhesive sheet.

In the embodiment described above, the shape of the base is substantially rectangular in plan view, but the shape in plan view is not limited thereto. The plan view shape may be any shape as long as it is possible to support the first conductive adhesive sheet and the second conductive adhesive sheet, and may have, for example, an elliptical shape, a perfect circular shape, a square shape, a diamond shape, a gourd shape, or a penta- or higher polygonal shape.

In the embodiment described above, the shape of the opening of the base is substantially rectangular in plan view, but the shape in plan view is not limited thereto. For example, the shape may have an arbitrary shape such as an elliptical shape, a perfect circular shape, a square shape, a diamond shape, a gourd shape, or a penta- or higher polygonal shape.

In addition, in the embodiment described above, the base is formed in a frame shape, but the present invention is not limited thereto. For example, the first conductive adhesive sheet and the second conductive adhesive sheet may be supported by an elongated rectangular base. A single elongated rectangular base described above may be provided, or two or more may be provided.

However, from the viewpoint of increasing the integrity of the components of the pad for electrodes and further improving the handling, it is preferable that the base has a frame shape.

In addition, for example, the base 10 may be provided with an extended portion extended in the longitudinal direction of one of the pads for electrodes, and a grip portion may be provided in the extended portion. Providing the grip portion enables the pad for electrodes to be peeled off easily from the object to be measured or the electrode of the sensor.

Here, optionally, the base 10 may be formed so as to extend in both longitudinal directions of the pad for electrodes or may be formed to extend in one or both of the lateral directions.

In addition, an opening may be formed in the extended portion provided as described above. This opening may be a window in which the optical sensor of the sensor and the image sensor are positioned. Alternatively, this opening may be utilized as a grip portion of the pad for electrodes.

Furthermore, optionally, the base 10 may be formed so as to extend in both longitudinal directions of the pad for electrodes or may be formed so as to extend in one or both of the lateral directions, and the opening may be suitably provided in the extended portion.

Here, the pad for electrodes may or may not have a window portion.

A release sheet may be provided on the surfaces of the first and second conductive adhesive sheets. When a release sheet is provided, it is possible to prevent the adhesion of foreign matter or the like to the surfaces of the first and second conductive adhesive sheets. This release sheet is peeled off from the surfaces of the first and second conductive adhesive sheets when the pad for electrodes is used.

The release sheet is not particularly limited, but is preferably made of a material or has a surface which can be easily released from the first and second conductive adhesive sheets. As the release sheet, for example, a sheet or a film formed of a thermoplastic resin is preferable, among which a polyethylene terephthalate film and a polypropylene film are more preferable. In addition, the release sheet may be subjected to a release treatment with silicone or the like on its surface to be contacted with the first and second conductive adhesive sheets.

Providing the pad for electrodes with a grip portion is preferable because the grip portion makes it to easily to peel off the release sheet before using the pad for electrodes.

When the adhesion between the first and second conductive adhesive sheets of the pad for electrodes and the sensor is not sufficient, an adhesive layer formed with a double-sided tape or the like may be provided between these components. This adhesive layer is preferably formed of a biocompatible material used for skin application.

The pad for electrodes of the present invention may be used not only for biometric sensors but also for industrial sensors.

Examples of industrial sensors include a sensor for detecting the surface resistance value of an object to be measured, a temperature sensor, an acceleration sensor, a sensor for simultaneously detecting a plurality of types of information such as a surface resistance and a surface temperature, an ultrasonic sensor, an image sensor, and the like.

EXAMPLES

Hereinbelow, the present invention will be described in more detail referring to the Examples; which however should not be construed as limiting the present invention.

The materials used in the Examples are as follows.

<Adhesive Sheet>

A-1: Product name "AG" produced by Sekisui Plastics Co., Ltd. Initial sheet thickness: 0.80 mm.

A-2: Product name "AG" produced by Sekisui Plastics Co., Ltd. Initial sheet thickness: 0.40 mm.

A-3: Product name "SR-A" produced by Sekisui Plastics Co., Ltd. Initial sheet thickness: 0.75 mm.

A-4: Product name "Mayclean-gel MGCS50" produced by Kyodo Giken Chemical Co., Ltd. Initial sheet thickness: 0.50 mm.

A-1 to A-3 are conductive adhesive sheets, and A-4 is a non-conductive adhesive sheet.

The non-conductive adhesive sheet refers to an adhesive sheet which is in a state where the resistance is too high such that resistance cannot be measured (i.e., in an insulated state) when the measurement is performed with respect to a measurement sample prepared by cutting the adhesive sheet into a piece of 50 mm×50 mm and storing the piece in a thermo-hygrostat chamber at 23° C. and a relative humidity of 50% RH for 24 hours. The measurement of the resistance is performed in the same manner as described above for [Resistance Measurement Method] except that the measurement target is the measurement sample described above.

<Base>

B-1: Product name "6670-1A" produced by Shinwa Corp. Thickness: 0.49 mm.

B-2: Product name "TT-70" produced by Daiwabo Polytech Co., Ltd. Thickness: 0.67 mm.

B-3: Product name "Carbon sheet NH-3". Thickness: 0.05 mm.

B-4: Product name "9825-8F" produced by Shinwa Corp. Thickness: 0.10 mm.

B-5: Product name "Syntex MY R 004" produced by Mitsui Chemicals, Inc. Thickness: 0.10 mm.

B-6: Product name "Tricot Half" produced by Inoue Knit. Thickness: 0.20 mm.

B-7: Product name "FM 070" produced by Kuraray Trading Co., Ltd. Thickness: 0.18 mm.

The thickness compressibility and the thickness recovery ratio of each adhesive sheet were measured according to the [Thickness Compressibility Measurement Method] and [Thickness Recovery ratio Measurement Method] described above. The results are shown in Table 1.

The water absorption capacity of each base was measured according to the [Method for Measuring Water absorption capacity] described above. The results are shown in Table 1. In addition, with respect to each base, the resistance of the base before immersion and the base after immersion was measured according to the above [Resistance Measurement Method]. When the resistance was not able to be measured (insulated state), the result was evaluated as "O", and when the resistance was able to be measured, the result was evaluated as "X". The results are shown in Table 1.

According to the [Method for Measuring Moisture Permeability] described above, a laminate was produced in which each adhesive sheet and each base were superimposed with the combinations shown in Table 1, and the moisture permeabilities thereof were measured. The results are shown in Table 1.

Examples 1 to 7 and Comparative Examples 1 to 7

Each of the adhesive sheets and bases was combined as shown in Table 1 to produce pad for electrodes in the form shown in FIG. 1.

When using the pad for electrodes of each Example, evaluation was carried out as follows as to whether fluctuation of the resistance of pad for electrodes was suppressed and stable measurement was possible (measurement stability), and whether or not stuffiness/rashes were able to be suppressed (suppression of stuffiness/rashes). The respective evaluation results are shown in Table 1.

[Method for Evaluating Measurement Stability]

The pad for electrodes of each Example was attached to an electrode of a commercially available biometric sensor in a manner as shown in FIG. 4 and the pad was attached, on its exposed surface without such an electrode of the biometric sensor, to the chest of a subject. Electrocardiography measurement was performed for 1 hour in this state. 30 minutes after initiating the measurement, the top surface of the biometric sensor was pressed with a finger for 2 minutes to apply an external force to the pad for electrodes to determine whether or not the electrode was short-circuited. Furthermore, 40 minutes after initiating the measurement, 20 mL of water was sprayed as mist centered on the pad for electrodes to simulate perspiration, so as to determine whether or not the electrode was short-circuited at that time. Then, the measurement stability was evaluated according to the following criteria, and the evaluation "O" was regarded as acceptable.

(Criteria for Measurement Stability Determination)

O: Fluctuation of the resistance of the pad for electrodes was suppressed, the electric signals from the subject were accurately transmitted to the electrode, and stable measurement was possible.

X: Fluctuation of the resistance of the pad for electrodes was large, the electric signals from the subject were not able to be accurately transmitted to the electrode and stable measurement was not possible. Alternatively, electrodes connected to the pad for electrodes were short-circuited.

[Method for Evaluating Suppression of Stuffiness and Rashes]

The pad for electrodes of each Example was attached to the skin of a chest degreased with ethanol and the pad was left as it was continuously for 12 hours per day. This operation was repeated for 3 consecutive days. The state of the skin before attachment of the pad, the state of the skin after three consecutive days of adhesion, and the state of stuffiness felt while the pad was attached were observed, and the suppression of stuffiness and rashes was evaluated according to the following criteria. The evaluation "O" was regarded as acceptable.

(Criteria for Suppressibility of Stuffiness/Rashes)

O: The skin condition after attachment of the pad for 3 days was the same as before the attachment.

X: Rashes are observed on the skin after attachment of the pad for 3 days. Alternatively, stuffiness was felt during the 3 days of attachment of the pad.

TABLE 1

| | | | Examples | | | | | | |
|---|---|---|---|---|---|---|---|---|---|
| | | | 1 | 2 | 3 | 4 | 5 | 6 | 7 |
| Pad for electrodes | Adhesive sheet | Type | A-1 | A-2 | A-3 | A-1 | A-1 | A-1 | A-1 |
| | | Initial sheet thickness (mm) | 0.80 | 0.40 | 0.75 | 0.80 | 0.80 | 0.80 | 0.80 |
| | | Compressed sheet thickness (mm) | 0.75 | 0.36 | 0.71 | 0.75 | 0.75 | 0.75 | 0.75 |
| | | Recovered sheet thickness (mm) | 0.79 | 0.39 | 0.74 | 0.79 | 0.79 | 0.79 | 0.79 |
| | | Thickness compressibility (%) | 6.25 | 10.00 | 5.33 | 6.25 | 6.25 | 6.25 | 6.25 |
| | | Thickness recovery ratio (%) | 98.8 | 97.5 | 98.7 | 98.8 | 98.8 | 98.8 | 98.8 |
| | Base | Type | B-1 | B-1 | B-1 | B-4 | B-5 | B-6 | B-7 |
| | | Water absorption capacity (times) | 1.1 | 1.1 | 1.1 | 1.4 | 1.3 | 1.3 | 1.4 |
| | | Resistance measurement results — Base before immersion | O | O | O | O | O | O | O |
| | | Resistance measurement results — Base after immersion | O | O | O | O | O | O | O |
| | Moisture permeability (g/m²/24 h) | | 3775 | 3851 | 3581 | 3765 | 3849 | 3891 | 1320 |
| Evaluation | Measurement stability evaluation results | | O | O | O | O | O | O | O |
| | Rashes/stuffiness suppression evaluation results | | O | O | O | O | O | O | O |

| | | | Comparative Examples | | | | | | |
|---|---|---|---|---|---|---|---|---|---|
| | | | 1 | 2 | 3 | 4 | 5 | 6 | 7 |
| Pad for electrodes | Adhesive sheet | Type | A-1 | A-1 | A-2 | A-2 | A-3 | A-3 | A-4 |
| | | Initial sheet thickness (mm) | 0.80 | 0.80 | 0.40 | 0.40 | 0.75 | 0.75 | 0.50 |
| | | Compressed sheet thickness (mm) | 0.75 | 0.75 | 0.36 | 0.36 | 0.71 | 0.71 | 0.49 |
| | | Recovered sheet thickness (mm) | 0.79 | 0.79 | 0.39 | 0.39 | 0.74 | 0.74 | 0.50 |
| | | Thickness compressibility (%) | 6.25 | 6.25 | 10.00 | 10.00 | 5.33 | 5.33 | 2.00 |
| | | Thickness recovery ratio (%) | 98.8 | 98.8 | 97.5 | 97.5 | 98.7 | 98.7 | 100 |
| | Base | Type | B-2 | B-3 | B-2 | B-3 | B-2 | B-3 | B-1 |
| | | Water absorption capacity (times) | 4.9 | 1.0 | 4.9 | 1.0 | 4.9 | 1.0 | 1.1 |
| | | Resistance measurement — Base before immersion | O | X | O | X | O | X | O |

TABLE 1-continued

|  |  |  |  |  |  |  |  |  |
|---|---|---|---|---|---|---|---|---|
|  | results | Base after immersion | X | X | X | X | X | X | ○ |
|  |  | Moisture permeability (g/m²/24 h) | 3641 | 50 | 3798 | 50 | 3407 | 50 | 352 |
| Evaluation | Measurement stability evaluation results | | X | X | X | X | X | X | X |
|  | Rashes/stuffiness suppression evaluation results | | ○ | X | ○ | X | ○ | X | X |

From the results shown in Table 1, it was confirmed that the pads for electrodes of Examples 1 to 7 according to the present invention suppressed fluctuation of resistance and are excellent in measurement stability. In addition, the pads for electrodes of Examples 1 to 7 did not cause stuffiness or rashes.

On the other hand, in the pad for electrodes (Comparative Examples 1, 3, and 5) in which a base that did not satisfy the water absorption capacity required in the present invention was used, stable measurement was able to be performed until 40 minutes after initiating the measurement; however, when water was sprayed to simulate perspiration at 40 minutes after initiating the measurement, the electrodes connected to the pad for electrodes were short-circuited and favorable measurement stability was not able to be obtained. In the pad for electrodes (Comparative Examples 2, 4, and 6) in which a conductive base was used and which did not satisfy the moisture permeability required in the present invention, the electrodes connected to the pad for electrodes were short-circuited and electrocardiographic measurement was not possible, and it was also not possible to suppress stuffiness/rashes. In the pad for electrodes (Comparative Example 7) using a non-conductive adhesive sheet and not satisfying the moisture permeability required in the present invention, electrocardiographic measurement was not possible and furthermore, it was not possible to suppress stuffiness and rashes.

From the above results, it was confirmed that the pad for electrodes according to the present invention was free from the risk of short circuits or the like, thereby ensuring stable measurement, and was unlikely to cause stuffiness or rashes. In addition, since the pads for electrodes of Examples 1 to 7 were able to be handled as an integral single unit, the handling thereof was excellent.

REFERENCE SIGNS LIST

1 PAD FOR ELECTRODES
2 FIRST CONDUCTIVE ADHESIVE SHEET
4 SECOND CONDUCTIVE ADHESIVE SHEET
10 BASE
12 OPENING
20 WINDOW
30, 32 ELECTRODE
34 OPTICAL SENSOR
36 IMAGE SENSOR

The invention claimed is:

1. A pad for electrodes comprising:
a first conductive adhesive sheet for connection with an electrode;
a second conductive adhesive sheet for connection with another electrode, said second conductive adhesive sheet positioned to be spaced apart from the first conductive adhesive sheet in a planar direction of the first and second conductive adhesive sheets; and
a base supporting the first conductive adhesive sheet and the second conductive adhesive sheet,
wherein the base overlaps a part of the first conductive adhesive sheet and a part of the second conductive adhesive sheet,
wherein at least one surface of each of the first conductive adhesive sheet and the second conductive adhesive sheet is exposed,
wherein each of the first conductive adhesive sheet and the second conductive adhesive sheet has a thickness compressibility of 10% or less and a thickness recovery ratio of 95% or more,
wherein the base comprises a non-electroconductive base having a water absorption capacity of 1 to 1.5 times,
wherein the pad has a moisture permeability of 1,000 g/m²/24h or more as measured with respect to a region where the base overlaps a part of the first conductive adhesive sheet and a part of the second conductive adhesive sheet, and
wherein the pad is configured to attach to skin.

2. The pad for electrodes according to claim 1, wherein each of the first conductive adhesive sheet and the second conductive adhesive sheet has both surfaces thereof exposed.

3. The pad for electrodes according to claim 2, wherein one or both of the first conductive adhesive sheet and the second conductive adhesive sheet is an acrylamide-based hydrogel.

4. The pad for electrodes according to claim 2, wherein the base is a woven fabric or a nonwoven fabric.

5. The pad for electrodes according to claim 2, wherein the base includes an opening through which the at least one surface of each of the first conductive adhesive sheet and the second conductive adhesive sheet is exposed and arranged to attach to a biometric sensor.

6. The pad for electrodes according to claim 1, wherein one or both of the first conductive adhesive sheet and the second conductive adhesive sheet is an acrylamide-based hydrogel.

7. The pad for electrodes according to claim 6, wherein the base is a woven fabric or a nonwoven fabric.

8. The pad for electrodes according to claim 6, wherein the base includes an opening through which the at least one surface of each of the first conductive adhesive sheet and the second conductive adhesive sheet is exposed and arranged to attach to a biometric sensor.

9. The pad for electrodes according to claim 1, wherein the base is a woven fabric or a nonwoven fabric.

10. The pad for electrodes according to claim 9, wherein the base includes an opening through which the at least one surface of each of the first conductive adhesive sheet and the second conductive adhesive sheet is exposed and arranged to attach to a biometric sensor.

11. The pad for electrodes according to claim 1, wherein the base includes an opening through which the at least one surface of each of the first conductive adhesive sheet and the second conductive adhesive sheet is exposed and arranged to attach to a biometric sensor.

* * * * *